(12) United States Patent
Spanjaard

(10) Patent No.: US 7,888,044 B2
(45) Date of Patent: Feb. 15, 2011

(54) MELANOMA BIOMARKER AND METHODS OF USES

(75) Inventor: Remco A. Spanjaard, Brookline, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 12/296,378

(22) PCT Filed: Apr. 10, 2007

(86) PCT No.: PCT/US2007/008835

§ 371 (c)(1), (2), (4) Date: Oct. 7, 2008

(87) PCT Pub. No.: WO2007/120658

PCT Pub. Date: Oct. 25, 2007

(65) Prior Publication Data

US 2009/0202545 A1    Aug. 13, 2009

Related U.S. Application Data

(60) Provisional application No. 60/790,717, filed on Apr. 10, 2006.

(51) Int. Cl.
*G01N 33/53* (2006.01)
*C12Q 1/68* (2006.01)

(52) U.S. Cl. ............................................. 435/7.1; 435/6
(58) Field of Classification Search ....................... None
See application file for complete search history.

(56) References Cited

FOREIGN PATENT DOCUMENTS

| WO | 9913078 A1 | 3/1999 |
|---|---|---|
| WO | 01058954 A3 | 8/2001 |
| WO | WO 01/58954 A2 * | 8/2001 |

OTHER PUBLICATIONS

Tockman et al (Cancer Res., 1992, 52:2711s-2718s).*
Stein et al (Cancer Research, Apr. 2004, 64:2805-2816).*
Hisaoka et al (Glia, 2004, 45: 313-324).*
Spanjaard, Remco A. et al., "Tumor necrosis factor superfamily member TROY is a novel melanoma biomarker and potential therapeutic target." Int J Cancer 120:1304-1310, 2007.
Torabain, S. and Kashani-Sabet, M., "Biomarkers for melanoma." Curr Opin Oncol 17:167-171, 2005.
Atallah, E and L Flaherty, "Treatment of Metastatic Malignant Melanoma." Current Treatment Options in Oncology 6:185-193, 2005.
Byers, HR et al., "Cell Migration and Actin Organization in Cultured Human Primary, Recurrent Cutaneous and Metastatic Melanoma." American Journal of Pathology 139(2):423-435, 1991.
Chambaut-Guérin, A-M et al., "Tumor Necrosis Factor Receptors in Neuroblastoma SKNBE Cells and Their Regulation by Retinoic Acid." Journal of Neurochemistry 65:537-544, 1995.
Curtin, Ja et al., "Distinct Sets of Genetic Alterations in Melanoma." N Engl J Med 353(20):2135-2147, 2005.
Eby, MT et al., "TAJ, a Novel Member of the Tumor Necrosis Factor Receptor Family, Activates the c-Jun N-terminal Kinase Pathway and Mediates Caspase-independent Cell Death." The Journal of Biological Chemistry 275 (20):15336-15342, 2000.
Gilchrest, BA, "Relationship between Actinic Damage and Chronologic Aging in Keratinocyte Cultures of Human Skin." The Journal of Investigative Dermatology 72:219-223, 1979.
Hisaoka, T et al., "Expression of a Member of Tumor Necrosis Factor Receptor Superfamily, TROY, in the Developing Olfactory System." GLIA 45:313-324, 2004.
Hisaoka, T et al., "Expression of a member of tumor necrosis factor receptor superfamily, TROY, in the developing mouse brain." Developmental Brain Research 143:105-109, 2003.
Hu, S et al., "Characterization of TNFRSF19, a Novel Member of the Tumor Necrosis Factor Receptor Superfamily." Genomics 62:103-107, 1999.
Kojima, T et al., "TROY, a Newly Identified Member of the Tumor Necrosis Factor Receptor Superfamily, Exhibits a Homology with Edar and Is Expressed in Embryonic Skin and Hair Follicles." The Journal of Biological Chemistry 275 (27):20742-20747, 2000.
Li, N. et al., "New prognostic factors of cutaneous melanoma: a review of the literature." Journal of Cutaneous Pathology 29:324-340, 2002.
Locksley, RM et al., "The TNF and TNF Receptor Superfamilies: Integrating Mammalian Biology." Cell 104:487-501, 2001.
Mandemakers, WJ and BA Barres, "Axon Regeneration: It's Getting Crowded at the Gates of TROY." Current Biology 15(8):R302-R305, 2005.
Mangini, J et al., "Immunohistochemical Markers of Melanocytic Lesions." The American Journal of Dermatopathology 24(3):270-281, 2002.
Naito, A et al., "TRAF6-deficient mice display hypohidrotic ectodermal dysplasia." PNAS 99(13):8766-8771, 2002.

(Continued)

*Primary Examiner* — Sean E Aeder
(74) *Attorney, Agent, or Firm* — Nixon Peabody LLP

(57) ABSTRACT

The present invention relates to the use of TROY, also called tumor necrosis factor receptor superfamily, member 19 (TNFRSF 19) also called toxicity and JNK inducer (TAJ), in diagnosis and therapy of non-epithelial cancers, such as melanoma. Accordingly, the invention provides in vitro and in vivo diagnostic and/or prognostic methods for cancers, other than epithelial cancers, preferably melanoma, comprising analyzing TROY expression in a biological sample from an individual or in an individual, wherein expression of TROY in non-epithelial cells, such as in melanocytes, in indicative the biological sample or the individual containing malignant cells, such as malignant melanoma cells. The invention also provides therapeutic use of TROY targeting molecules, such as TROY antibodies or TROY targeting RNA interfering agents for treatment of cancer wherein the cancer cells express TROY.

9 Claims, 6 Drawing Sheets

OTHER PUBLICATIONS

Ohazama, A et al., "Traf6 is Essential for Murine Tooth Cusp Morphogenesis." Developmental Dynamics 229:131-135, 2004.

Parmiani, G et al., "Immunotherapy of melanoma." Seminars in Cancer Biology 13:391-400, 2003.

Pispa, J et al., "Ectodysplasin, Edar and TNFRSF19 are expressed in complementary and overlapping patterns during mouse embryogenesis." Gene Expression Patterns 3:675-679, 2003.

Sinha, SK et al., "Role of TRAF3 and -6 in the Activation of the NF-kB and JNK Pathways by X-linked Ectodermal Dysplasia Receptor." The Journal of Biological Chemistry 277(47):44953-44961, 2002.

Spanjaard, RA et al., "Clone 10d/BM28 (CDCL1), an Early S-Phase Protein, is an Important Growth Regulator of Melanoma." Cancer Research 57:5122-5128, 1997.

* cited by examiner

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 1
gcaagaattc agggatcggt ctgg                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 2
agcgctgcag ataacggcag ccag                                              24

MELANOMA BIOMARKER AND METHODS OF USES

CROSS-REFERENCE TO RELATED APPLICATIONS

This application is a National Phase Entry Application under 35 U.S.C. §371 of co-pending International Application PCT/US2007/008835, filed 10 Apr. 2007, which claims benefit of U.S. provisional application No. 60/790,717, filed on 10 Apr. 2006, the content of which is incorporated herein by reference in its entirety.

GOVERNMENT SUPPORT

This invention was made with Government Support under Contract Nos. CA76406 and CA105511 awarded by the National Institutes of Health. The Government has certain rights in the invention.

BACKGROUND OF THE INVENTION

Skin cancer or melanoma is the most commonly found type of cancer. Even though melanoma represents only 4% of the total number of cases, it is responsible for about 79% of cancer deaths. According to statistics provided by the American Cancer Society, in contrast to many other types of cancers, the number of new cases of melanoma in the United States is still on the rise, currently at the rate of about 3% a year.

In the past three decades, virtually no therapeutic advances have been made that would increase the survival rate of patients with late stage of melanoma. The current survival rate is about 3-9%, As with all cancers, it is imperative to catch melanoma early. About 70% of melanomas are "superficial spreading", meaning that they undergo a superficial, radial growth phase before they grow vertically and invade underlying tissue, a much more serious condition. Unfortunately, about 20% of cutaneous melanomas immediately start out with a vertical growth phase, which explains why these tumors are so dangerous. The 5-year survival rate for Stage 1 melanoma is very good, about 80-95%. However, this drops off rapidly when cancer is allowed to progress and invade, first locally and then more distantly. Survival rate for Stage 2 disease is only 40-80%, Stage III 10-70% and Stage 4 is almost invariable lethal within 5 years (<5-10% survives beyond 5 years) due to untreatable distant metastasis to especially lung and brain.

Melanoma originates from malignant transformation of melanocytes, the pigment producing skin cells, via atypical and dysplastic premalignant intermediate stages to locally invasive and finally metastatic melanoma. A large number of genes have been implicated to play a role in these processes such as H-Ras, bFGF, c-Kit/SCF and EGFR. Recently, attention has focused on p14ARF and the CDK inhibitor p16INK4a which was identified as a susceptibility gene in familial melanoma. Many other factors are likely involved.

Melanoma is one of most difficult malignancies to classify histologically. This contributes greatly to its problematic diagnosis, prognosis and treatment.

For the pathologist, the best prognostic indicator available currently is the depth or vertical growth of the lesion, i.e. tumor thickness, which is clearly associated with a poor prognosis. However, the tumor itself can present a real problem because it is typically heterogenous even within the same lesion. The cells can have many different sizes, shapes and colors, making it often difficult to pinpoint the diagnosis. The histological determination of melanoma is even more difficult with atypical melanocytes. Such melanocytes can either be completely benign, or they can be premalignant with a high probability of progressing into melanoma, which greatly hampers the accuracy of diagnostic and treatment decisions offered to the patient.

To assist the dermatopathologist in his diagnosis, currently available tools include, for example, morphometry, DNA ploidy, chromosome and nucleolar organizing analyses.

However, immunohistochemistry, which uses specific antibodies generated against melanoma-associated proteins to find whether specific markers are expressed in suspect tissue remains the preferred technique because it is relatively simple, it can be automated, it is quick, reproducible and commonly used in modern hospitals.

A large variety of these molecular "melanoma biomarkers" have been identified, and while most have been found to be of no or only limited value in the clinic, there are some, e.g. MCAM, S100, TRP1 and gp100/HMB45 that are used on a routine basis in the attempts to establish a melanoma diagnosis. Another marker is MiTF (micro-ophthalmia tissue factor). To increase the value and reliability of these markers, typically a panel of different markers is used. This consumes more time and finances than if a single antibody could be used. Moreover, even the results derived from panels of markers is often not of sufficient enough quality to make a reliable diagnosis. Specifically, metastasizing tumors can present a problem because they are even more heterogenous than primary tumors, making them difficult to analyze. Additionally, there is also no specific marker for atypical and potentially premalignant melanocytes that can distinguish them from benign melanocytes. These are significant problems facing dermatology pathologists.

The typical treatment option for melanoma patients is surgery, which is highly effective when the tumor is still local and in its radial growth phase. If the tumor is more invasive, surgery can be combined with radiation and/or chemotherapy. Since these conventional modalities cannot cure patients of lethal metastasized tumors, efficacy of alternative treatments such as immunotherapy are being investigated in clinical trials. However, currently there is essentially still no cure for advanced stage disease despite decades of research.

Metastatic melanoma, the usual cause of death, is notoriously resistant to conventional therapy, and only improved understanding of the genetics of this disease can be expected to lead to new therapeutic breakthroughs. Although much progress has been made in this regard (1), few, if any, significant new pharmacologic targets or therapies have come to the clinic. Immuno and biochemotherapy remain the most promising strategies (2,3), although even here the scarcity of tumor-specific cell surface proteins has largely prevented development of antibody-based therapies (3).

Thus, more targets, ideally those on the cell surface, are urgently needed for both diagnostic and various types of intervention therapies.

SUMMARY OF THE INVENTION

The present invention relates to the use of TROY (also called tumor necrosis factor receptor superfamily, member 19 (TNFRSF 19) also called toxicity and JNK inducer (TAJ)) in diagnosis and therapy of non-epithelial cancers, such as melanoma.

In one embodiment, we have discovered that TROY is a highly reliable marker to diagnose a malignant melanocyte.

In another embodiment, we have discovered that one can target and destroy malignant non-epithelial cells, such as malignant melanocytes by targeting TROY, a single transmembrane protein expressed in non-epithelial cancer cells.

Accordingly, in one embodiment, the invention provides a diagnostic and/or prognostic method for cancers, other than epithelial cancers, preferably melanoma, comprising analyzing TROY expression in a biological sample from an individual, wherein expression of TROY in cells, such as melanocytes, in indicative of cancer, such as melanoma.

In one embodiment, TROY protein is detected in the biological sample using immunological methods, such as immunohistochemistry. The biological sample can be a blood sample, a tissue sample or any other sample containing cells from a human. The antibody can be a polyclonal or monoclonal antibody that recognizes an immunogenic fragment of TROY. In one embodiment, the immunogenic fragment is in the extracellular portion of TROY. In another embodiment, the immunogenic fragment is an intracellular portion of TROY. In one preferred embodiment, the immunogenic fragment comprises amino acids that are not part of the domains homologous to the tumor necrosis factor domains.

In another embodiment, one detects TROY expression using nucleic acid detection methods, preferably RNA detection techniques, such as RT-PCR-based methods.

In one embodiment, one looks at increased TROY expression, either at nucleic acid or protein level, relative to a control cell or sample of the same biological tissue origin. For example, on can set up a baseline level for what a normal expression is in any particular tissue sample of human cells. One can also set up controls based on the expression amount of TROY in different the types and/or stages of malignancy, such as melanoma. Thus, in one embodiment, one can screen for individuals or monitor an individual, such as individual who is at high risk of developing melanoma by measuring TROY expression in a tissue sample. The screening and/or monitoring can be part of a routine check-up or part of a routine dermatologist screen. For example, in a screening of an individual for melanoma, increased expression of TROY in indicative of having melanoma.

In one embodiment, the invention provides a method for treatment of cancer, preferably non-epithelial cell cancers such as melanoma, by administering to an individual in need thereof, a TROY-targeting agent such as an antibody or a vector encoding TROY or an antigenic epitope thereof. One may also use RNA interfering agents, or antisense oligonucleotides that are targeted against TROY. In another embodiment, the antibody to TROY delivers an antitumor agent, such as a toxic molecule to the cell expressing TROY.

| Lane | Cells | Tissue type | TROY expression | Notes |
|------|-------|-------------|-----------------|-------|
| 1 | melanocytes | normal cells | − | melanotic |
| 2 | SK-Mel-2 | melanoma | +++ | melanotic |
| 3 | SK-Mel-3 | melanoma | +++ | melanotic |
| 4 | Hs695t | melanoma | +++ | amelanotic |
| 5 | C32 | melanoma | +++ | amelanotic |
| 6 | A375 | melanoma | ++ | amelanotic |
| 7 | MCF-7 | breast carcinoma | − | |
| 8 | MDA-MB-231 | breast carcinoma | −/+ | |
| 9 | MDA-MB-435s | breast carcinoma | −/+ | |
| 10 | Hela | cervical carcinoma | − | |
| 11 | OV4 | ovarian carcinoma | − | |
| 12 | OV7 | ovarian carcinoma | − | |
| 13 | SCC-9 | head and neck SCC | − | |
| 14 | SCC-15 | head and neck SCC | − | |
| 15 | SCC25 | head and neck SCC | − | |
| 16 | Fadu | head and neck SCC | − | |
| 17 | Hep 3B | hepatocellular carcinoma | − | |
| 18 | P3HR-1 | Burkitt lymphoma | − | |
| 19 | 293 | embryonal kidney | + | |

Figure 3A:
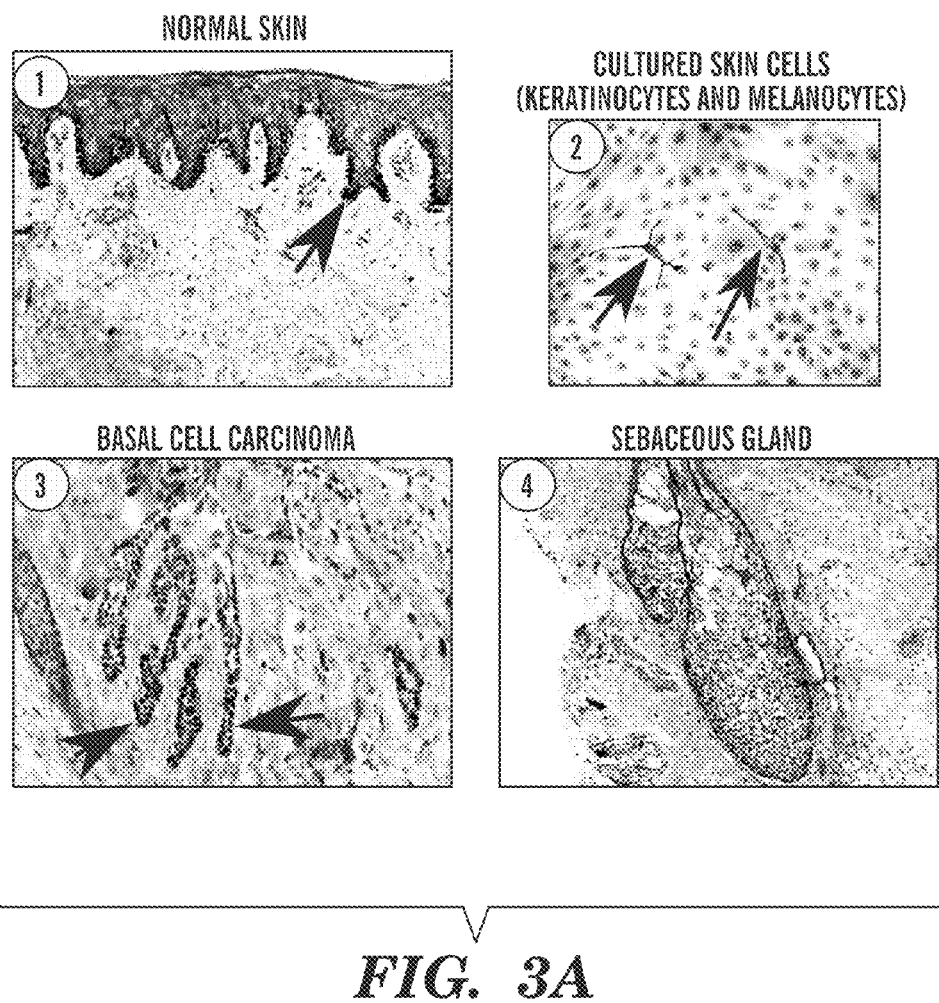
Figure 3B:
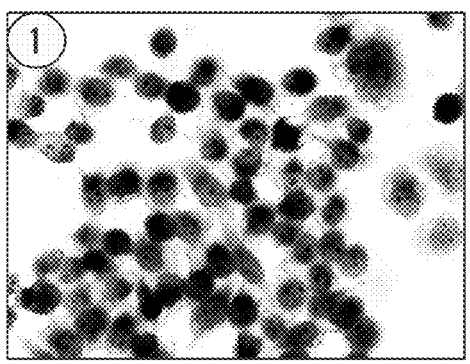
Figure 3B:
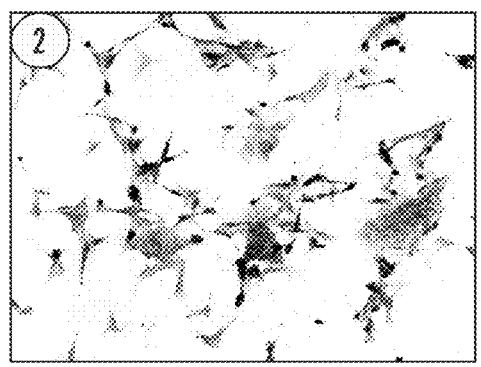
Figure 3C:
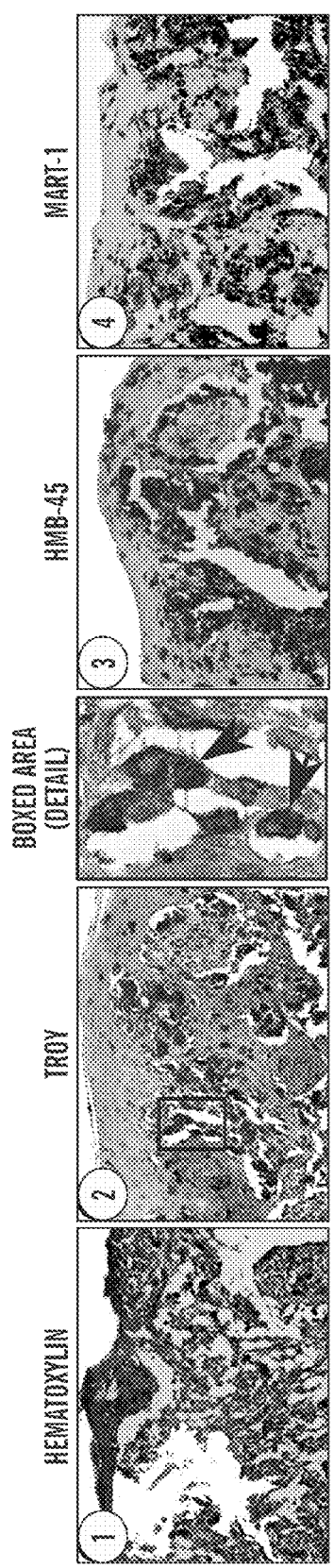
Figure 3D:
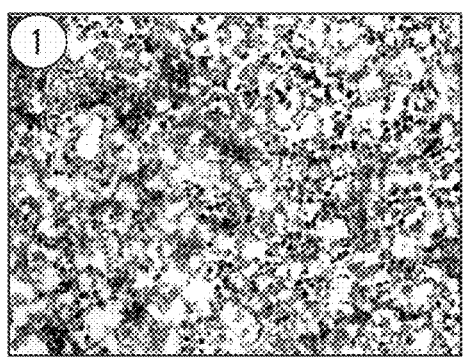
Figure 3D:
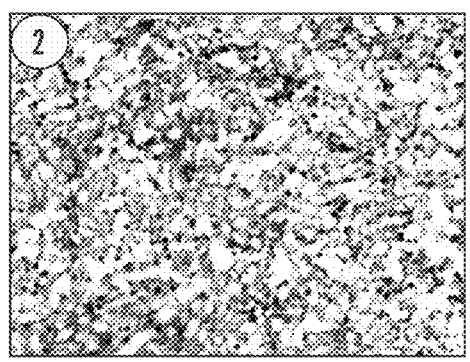

FIGS. 3A-3D show an immunohistochemical analysis showing that TROY is specifically re-expressed at high levels in melanoma. TROY-signaling is likely functional in these tumors because TROY and TRAF-6 are co-expressed. Representative samples of various tissues and cells stained with various antibodies, or hematoxylin (Magn., ×20. See below for overview of staining results. FIG. 3A shows that negative TROY-staining is found in normal skin biopsies that include epidermal melanocytes (panel 1, arrow), and also cultured normal primary skin that consist of keratinocytes mixed with melanocytes (panel 2, arrows). BCC (panel 3, arrows) samples are also negative although moderately strong TROY staining is observed in sebaceous glands (panel 4). FIG. 3B shows that in contrast to normal skin constituents, strong TROY staining is detected in primary cells derived from a primary (panel 1) and metastatic (panel 2) melanoma. FIG. 3C shows that melanoma (paraffin-embedded) tissue samples are also strongly positive for TROY as illustrated by staining of a serial section of this tumor (panel 1, hematoxylin-stained for reference; panel 2, TROY-staining). The area in the indicated box is enlarged to provide more detail and intense cytoplasmic staining of individual tumor cells (indicated by arrows) can be appreciated (panel 2). Additional sections were also found to be positive for widely-used melanoma biomarkers HMB-45 (panel 3) and MART-1 (panel 4). FIG. 3D shows another serial (fresh frozen) section from a different tumor shows co-expression of TROY (panel 1) and adapter molecule TRAF-6 (panel 2). We note, that infiltrating lymphocytes remain unstained, which in was indicated by a blue color in panels 1 and 2 in the original slides.

| Tissue/cells | TROY (% positive) | TROY + TRAF-6 (% positive) |
|--------------|-------------------|----------------------------|
| Melanoma[1] | 45/45 (100)* | 10/10 (100) |
| Primary cultured melanoma cells[2] | 2/2 (100) | nd |
| Primary cultured keratinocytes + melanocytes | 0/1 (0) | nd |
| Normal skin | 0/10 (0)* | nd |

-continued

| Tissue/cells | TROY (% positive) | TROY + TRAF-6 (% positive) |
|---|---|---|
| Sebaceous glands[3] | 2/2 (100) | nd |
| Basal cell carcinoma | 0/6 (0)* | nd |

[1]three primary, 38 metastatic and four unclassified melanomas
[2]primary cells derived from one primary and one metastatic melanoma
[3]germinative cells
*$P < 0.0001$(by two-tailed Fisher's Exact Test)

Figure 4:
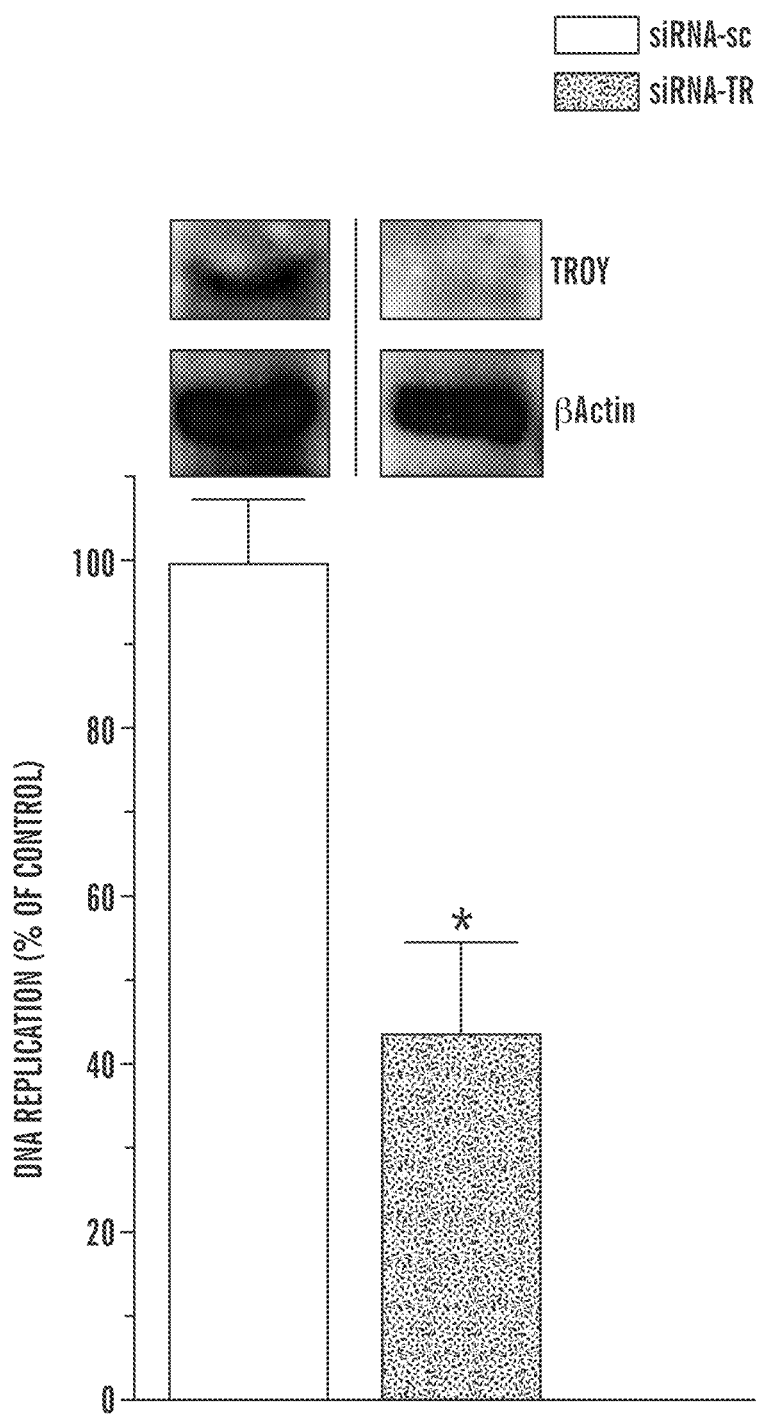

FIG. 4 shows that suppression of TROY expression reduces DNA replication in melanoma cell line SK-Mel-2. Cells transfected with an siRNA targeting TROY (siRNA-TR) but not a scrambled control siRNA (siRNA-sc) have reduced TROY expression as shown in immunoblot (top; βActin serves as loading and specificity control). DNA replication was determined by [3H]-thymidine incorporation assay and results are shown at the bottom panel. Proliferation was significantly reduced to about 50% in cells with low TROY expression relative to control cells. Shown is a representative experiment done in triplicate and repeated three times with similar results. Data are expressed as the mean±SD. *, $P \leq 0.004$ (by Student's t test analysis).

DETAILED DESCRIPTION OF THE INVENTION

The present invention is based upon our findings that TROY is specifically expressed in cancer or malignant cells, such as melanoma and gliosarcoma and other neuronal cell type-derived tumor cells, as well as prostate cancer cells. However, TROY is not typically expressed in other (skin) tumor cells such as epithelial tumor cells.

Accordingly, we have discovered that detecting TROY expression in these cells provides a novel diagnostic and/or prognostic biomarker, and it presents a novel target for anti-cancer therapies. The discovery that TROY is expressed by tumor cells, particularly non-epithelial tumor cells such as melanoma, gliosarcoma and other neuronal cell type-derived tumor cells, as well as prostate cancer cells, is also useful in immunotherapeutical approaches to treating cancers. On can use TROY as a melanoma-associated antigen to generate cytotoxic T cells directed against the TROY antigen-expressing tumor cells. We have now found that TROY belongs to the group of cancer-associated, for example, melanoma-associated antigens and can be used as well as any other published antigen used in detection and treatment of cancers, such as melanoma, prostate cancer, gliosarcoma and other neuronal cell type-derived tumor cells.

We have also shown that detection of TROY as a marker on the malignant cells provides a superior test to cancer cell detection when compared to detection of other cancer-associated antigens, such as melanoma associated antigens Mart-1 or HMB-45. This is due to the much more restricted expression pattern of TROY in the malignant cells compared to expression of any other tumor marker. Accordingly, detection of TROY in melanocytes in a biological sample provides more reliable diagnostic method. In one embodiment, one can replace a panel of other cancer markers with just detection of TROY to provide a diagnosis. In another embodiment, one can also include TROY as a part of a panel of other cancer markers to further increase the reliability of the diagnostic tests wherein other cancer markers are used.

By employing an in vitro screen for melanoma-associated genes, we identified a member of the tumor necrosis factor receptor superfamily (TNFRSF) called TROY. TROY, which is also a member of the ectodysplasin receptor subfamily. TROY is widely expressed during mouse embryogenesis, but in adults expression becomes restricted to hair follicles and specific brain regions. Thus far the only known biological role of TROY has been as a coreceptor of a neuronal receptor complex that mediates inhibition of axonal regeneration by myelin inhibitors. We believe that prior to our studies as described herein, TROY has not been associated with non-epithelial cancers, such as melanoma. Here, we determined that TROY is expressed in all primary and metastatic melanoma cells and tissue samples, with the exception of sebaceous glands. We also found that TROY is not expressed or not expressed at significant levels in normal skin biopsies and primary skin cell cultures that contain normal keratinocytes and melanocytes, nor is it typically expressed in other (skin) tumor cells such as epithelial tumor cells.

We also found that TROY signaling is functional and contributes to DNA replication in melanoma. Accordingly, targeting TROY provides a novel approach for treating non-epithelial cancer cells such as melanoma.

Thus we discovered that TROY, a member of the tumor necrosis factor receptor superfamily can be used as both a new biomarker for melanoma and a new cell surface target for the identification of compounds or drugs for the treatment of melanoma, including cell/or antibody-based therapies. TROY can also be used to target anti-tumor agents to cells that express TROY, such as to malignant melanocytes.

We found that none of 10 normal human skin biopsies and none of 6 human basal cell carcinoma specimens had detectable TROY expression but all 45 primary and metastatic melanoma patient samples were TROY-positive with high levels of cytoplasmic expression in individual tumor cells. Accordingly, one can detect melanoma using in vitro diagnostic as well as in vivo analysis of tissue samples. One can also use analysis of TROY expression in blood because the circulating tumor cells are often present in the blood circulation as well as in the immediate tumor mass.

We initially used murine S91 melanoma cells as a valuable in vitro model to clone melanoma-associated genes (4). In one of these screens we identified a type I transmembrane receptor member of the tumor necrosis factor receptor superfamily (TNFRSF) called TNFRSF expressed on the mouse embryo (TROY) (5) or alternatively, toxicity or JNK inducer (TAJ) (6) or TNFRSF19 (7) or TRADE, TAJ-ALPHA (GENEATLAS GENE DATABASE). TROY is also a member of the ectodysplasin (EDA) receptor (EDAR) subfamily that includes EDAR and X-linked EDAR (XEDAR). Hypohidrotic ectodermal dysplasia (HED) is a congenital disease that presents with sparse scalp hair, lack of sweat glands, and abnormal or missing teeth. HED is caused by mutations in EDA, EDAR or XEDAR and it is suspected that TROY also plays a role in this disease (8,9). It was recently established that TROY is a Nogo-66 receptor co-receptor that mediates inhibition of axonal regeneration by myelin inhibitors (10), however, it is our understanding that prior to our study, TROY has not been associated with melanoma.

We showed that TROY is typically expressed in all primary and metastatic melanoma cells and tissue samples, but not in normal melanocytes found in normal skin biopsies and primary skin cell cultures, nor is TROY detectable in other (skin) tumor cells. Accordingly, we provide a method of diagnosis and/or prognosis of cancer, specifically non-epithelial malignancies, such as melanoma, based on detecting whether TROY is or is not expressed in by the cells in a biological sample. If TROY is expressed, for example a skin biopsy sample, the sample comprises malignant non-epithelial cells.

Although we have determined that TROY is not present in normal melanocytes or most of the other normal cells in an adult, at least not nearly at the levels that we see it in the malignant cells, one can easily distinguish the non-epithelial cells using morphological analysis of the histological sample. For example, melanocytes, even if they are atypical melanocytes, have a typical morphology that can be observed, for example using histochemical analysis, such as a split-DOPA preparation. Accordingly, in one embodiment, one detects TROY expressing cells and one can also review the morphology of the cells to assist in determining that the cells are of non-epithelial origin, such as melanocytes.

If one detects TROY expression or increased TROY expression in a biological sample, that is indicative that the sample contains tumor cells, for example malignant melanoma cells. Thus an individual from whom the sample has been taken can be determined as carrying tumor cells.

TROY is a cell surface receptor. Thus, one can also look for shed TROY protein in a biological sample, for example, blood or urine sample to detect increase in TROY expression. Such a method is a non-invasive or relatively non-invasive method for detection of tumor cells, such as malignant melanoma cells.

We also showed that TROY signaling is functional and contributes to DNA replication in melanoma cells. Together, our data establish TROY as the first TNFRSF member that is a highly specific biomarker for non-epithelial cell cancers such as melanoma.

In one embodiment, the invention provides use of TROY also as a cell surface target for rational drug inhibitors, and cell and/or antibody-based immunotherapies.

We also demonstrated for the first time positive TROY staining of metastatic melanoma by immunohistochemical techniques.

TROY was cloned by others and its sequence, developmental expression in mice and activity in cultured cells are known (Kojima et al., J. Biol. Chem., Vol. 275, Issue 27, 20742-20747, Jul. 7, 2000). However, we believe that we are the first to show that TROY expression is linked to melanoma. We believe that we are the first to show and report TROY as a cancer biomarker and a therapeutic cancer target.

The term "melanoma" as used herein includes, but is not limited to skin cancers as described herein. There are four major types of melanoma that each constitute a distinct level of danger owing to their metastatic potential. "Superficial Spreading" is the most common form (70%) of melanoma in Caucasians, usually found on the trunk, upper arms and thighs but it can be anywhere on the body. It begins as a small pigmented, slightly raised asymmetric macule that has irregular borders, and can have many color variations. Superficially Spreading typically shows earlier signs of invasiveness than the following two types: "Lentigo" and "Maligna." Maligna is typically found in elderly people. It is similar to the superficial spreading type and is usually located on the head and neck region. It presents as a flat or slightly elevated mottled dark skin discoloration. It can remain restricted to the epidermis for long periods of time, but it remains potentially invasive (after which it is called Lentigo Maligna Melanoma).

Acral-Lentiginous Melanoma is more commonly found on the palm of hands, soles of feet, and nail beds in African-Americans and Asians. Like the previous two types, it starts out as a superficial spreading tumor that can resemble a wart or fungus. This phase is relatively long before it turns more invasive.

Nodular Melanoma is more often on the trunk, upper arms, and thighs. It is usually diagnosed when it is already invasive. Its color can vary greatly but is most often black. This type of melanoma may ulcerate and present as a non-healing skin ulcer.

Some less common melanoma variants include desmoplastic malignant melanoma, which is histologically ill-defined but it can involve normal stromal cells to varying degrees in its architecture. It has a high incidence of local recurrence and repeated surgical removal can increase the risk of metastasis. Giant Melanocytic Nevus is a birthmark (mole) of over 20 cm in diameter. They demand attention because there is a risk of up to 5% that they develop into melanoma. Amelanotic Malignant Melanoma simply means a tumor without pigment. Lack of dark color (they are usually pink or red) can make it more difficult to spot and recognize. Nevoid Melanoma is a melanoma with a deceptively benign looking histology, by resembling normal melanocytes.

There are a large number of other variants, even within recognized types mentioned here and they are all considered to be encompassed within the term "melanoma" as used in this application.

The term "biological sample" as used herein means any sample of biological origin that can be extracted, swiped or otherwise obtained from a human and that contains cells or proteins or nucleic acids. Such samples include but are not limited to tissue, tumor tissue, blood, serum, cells, cell cultures established from tissue, blood or cells obtained from an individual, buchal swabs, saliva, hair follicles, urine, stool, tears, bone marrow, and sputum.

TROY (or TAJ) was discovered in 2000 by two different groups. Since then it has also been called TRADE or TNFRSF19. It is a member of the tumor necrosis factor receptor superfamily (TNFRSF) which are type 1 transmembrane proteins. TROY is related to EDAR (ectodermal dysplasia receptor), another family member: EDAR mutations in humans result in ectodermal dysplasias: anomalies of the hair, teeth, nails, and sweat glands. Activation (by ligand or overexpression) of TROY and engagement of its intracellular adaptor proteins TRAF2 or 6 is accompanied by activation of the c-Jun N-terminal kinase pathway, NFkB and caspase-independent cell death (also called paraptosis) in a tissue-dependent manner.

Human TROY has at least two known splice variants that appear to differ slightly in their intracellular, carboxyl terminal portion. The TROY protein is a single pass transmembrane protein that has a 29 amino acid signal sequence (amino acids 1-29), and a region of amino acids 34-138 that is homologous with tumor necrosis factor (TNF) domain, extracellular regions that appear to be unique to TROY, namely, the amino acids 30-33, and 139-168, a transmembrane domain from amino acid 169-193, and an intracellular domain from amino acid 194 to 421 or in the second splice variant from 194 to 415.

In the embodiments of this invention where one uses antibodies against TROY for diagnostic purposes, one can select any immunogenic fragment of TROY peptides to raise an antibody as is well know to one skilled in the art. The fragments that are immunogenic will lead to generation of antibodies. TROY fragments can be readily screened for immunogenic activity. Preferably, one uses monoclonal antibodies, but one can also use polyclonal antibodies. One can perform an immunohistochemical analysis using a polyclonal or monoclonal antibody raised against the entire TROY peptide, or any fragments thereof. In one embodiment, one excludes the transmembrane domain from the immunogenic or antigenic fragments. In another embodiment, one uses only the extracellular part of the peptide as an antigen. In another embodiment, one uses the intracellular part of the TROY peptide as an antigen. In one embodiment one excludes the last 8 carboxyl terminal amino acids that differ between the splice variants. In another embodiment, one uses antibodies that are specifically raised against peptides that comprise the unique carboxyl terminal regions of the two splice variants. In yet another embodiment, one uses as antigens, TROY peptides that comprise the unique regions of TROY's extracellular domain. In one embodiment, one uses an antibody that is raised against a peptide that comprises a region that is encoded by the nucleic acid between the primers of SEQ ID NO: 1 and SEQ ID NO: 2 (primer sequence inclusive).

One uses TROY antibodies that are specific for TROY protein relative to other proteins. Thus, the antibodies useful according to the invention are antibodies that do not significantly cross-react with other proteins. How to accomplish this is well known to one skilled in the art. For example, after production of different antibodies, one can screen for antibodies that bind TROY but do not bind other related or unrelated proteins.

In one embodiment, the antibody is targeted to the extracellular regions of TROY that specifically recognizes TROY and typically does not substantially cross-react with other proteins. In one embodiment, the antibody is targeted against the intracellular regions of TROY. It is well known that intact transmembrane proteins can be shed from the membrane (Olsen et al., Biochem J. 1993 Nov. 1; 295(Pt 3): 833-840.) Thus, it is likely that in the biological samples that are used for the diagnostic and prognostic methods of the present invention to detect TROY, peptides that have exposed intracellular domains will likely be present.

For the treatment methods, one preferably targets the extracellular domain, and more preferably a domain that comprises all or part of the unique regions of TROY as described above.

The term "immunogenic fragment" of TROY means a TROY peptide fragment that generates an immune response (i.e., has immunogenic activity) when administered, alone or optionally with a suitable adjuvant, to an animal, such as a mammal, for example, a rabbit or a mouse, and also including a human.

Therapeutics that target the active fragments of TROY that serve as functional fragments in the signal transduction, such as the intracellular portion of TROY that interacts with TRAF-6, are preferred therapeutics. One can use antibodies, analogs, mimics, and the like to block or reduce TROY function, either at the signal transduction level or at the extracellular receptor-binding level in vivo.

As noted, the polypeptides, fragments or other derivatives of TROY, or analogs thereof, or cells expressing them, can be used as an immunogen to produce antibodies thereto.

For the nucleic acid based analysis methods, such as mRNA detection, one can design primers from any region of the mRNA, including the non-coding regions. Preferably one selects primers that can substantially distinguish TROY mRNA from other proteins expressed in the biological samples. Accordingly, regions that encode the unique polypeptide regions are preferred. For example, one can use primers that are selected from exon 2 or 3 of the TROY nucleic acid, for example SEQ ID NO: 1 and SEQ ID NO: 2. A skilled artisan can easily design and test other primers for specific TROY nucleic acid amplification or detection.

On can use the entire coding TROY nucleic acid or protein sequences or fragments thereof as probes for, for example Northern blot hybridization and in situ hybridization analyses. A skilled artisan can easily design optimal nucleic acid fragments and label them with a suitable detectable label.

Expression of TROY is highly restricted in adult tissues. TROY RNA was detected in the developing central nervous system, primarily the ventricular and subventricular zones which contain neuronal and glial precursors during mouse embryogenesis. TROY protein was found in some specific subsets of glial cells in the olfactory bulb in developing mice. Other studies showed that at day 13.5, TROY RNA is exclusively expressed in neuroepithelium in frontal and lateral lobes, epidermis of skin, bronchiolar epithelium, tongue epithelium, gastric epithelium, conjunctiva and cochlea. In neonates expression is restricted to hair follicles and neuron-like cells in the cerebrum.

Previously, less has been known about expression in humans, but RNA was detected at relatively high levels in adult human prostate gland and low to very low levels in spleen, thymus, testis, uterus, small intestine, colon, peripheral blood lymphocytes. Cell lines that express TROY are gliosarcoma cell lines GI-1 and U251, A3-1 embryonic stem cells, embryonal carcinoma cells NF-1, 293 (human embryonic kidney) and LNCaP prostate cancer cells. From the limited information that is available one can conclude that TROY expression is highly restricted in human adults, for example prostate and prostate and gliosarcoma cancer cells. One can look at changes in TROY expression levels in a biological sample to determine if the cell is malignant, such as a malignant melanoma cell. In one embodiment, one compares the expression level in a test biological sample to expression level in a control sample of substantially the same biological origin and, in one embodiment of substantially the same size. In one embodiment, the control sample is from an individual who does not carry malignant cells, preferably malignant melanoma cells. Increased expression of TROY is indicative that the test biological sample contains malignant cells, such as malignant melanoma cells.

Alternatively, the control sample is from an individual who carries a known type, and/or stage cancer, such a melanoma. In this case, one uses matching the TROY expression level of the test sample to the control sample, wherein the diagnosis in the control sample that most closely matches the test result is selected as a diagnosis for the test sample.

Our results showed that TROY is essentially only expressed in melanoma, but not benign melanocytes or epithelial cancer cells. Accordingly, in one embodiment TROY is used to detect cancers other than epithelial cell cancers.

TROY was expressed in human embryonic kidney cells 293, consistent with the published observations. However, expression levels during the embryonal development appear to be much higher in the melanoma cells.

*Homo sapiens* TROY protein sequence is described, for example in the NCBI Sequence Database AAQ89247 (GenBank with accession No. gi:37182894). *Homo sapiens* clone DNA84210 TROY (UNQ1888) mRNA, complete cds, can be found from the NCBI Sequence Database with accession No. AY358888. The nucleotide sequences for the mouse TROY, dTROY, a smaller cytoplasmic segment of TROY, and human TROY can be found in the DDBJ/GenBank™/EMBL Data Bank with accession numbers AB040432, AB040433, and AB040434, respectively. The published sequence AB040434 comprises the complete mRNA for human TROY. The protein sequence of the human TROY is available at DDBJ/GenBank™/EMBL Data Bank with Accession No. BAB03269.

Using the accessible sequence information using routine methods one can determine and test suitable PCR primers to amplify TROY nucleic acid fragments for the purposes of detecting TROY nucleic acids in a sample. Similarly, using the protein sequence, one can select fragments for making TROY-specific antibodies to detect TROY protein in a biological sample.

Diagnostic and Prognostic Methods

We have shown that cancer cells, other than epithelial cancer cells, and particularly melanoma, gliosarcoma and other neuronal tumors, as well as prostate cancer express TROY. We have shown that TROY stains cancers other than epithelial cancer cells, particularly melanoma with superior specificity for when compared to currently used markers (e.g., Mart-1 or HMB-45), and that it can positively stain all melanoma classes that often provide difficulties for at least some of the other markers. Accordingly, we believe that TROY can become a standard melanoma-staining tool for the dermato-pathologist by replacing what is now often a panel of several different markers. TROY can also serve as prognostic marker.

Accordingly, in one embodiment, the invention provides a diagnostic method for detecting cancer by analyzing nucleic acid and/or protein expression of TROY in a biological sample from an individual in need of cancer diagnosis.

Analysis of TROY expression can be performed with any known methods including use of antibodies or RNA detection methods. To the extent TROY is expressed in a cell other than a melanoma or benign melanoma cell, one can use other standard detection tools to enhance reliability. In addition, one can also look at the level of expression of TROY.

In one embodiment, the biological sample is treated as to prevent degradation of TROY protein or RNA, specifically mRNA encoding TROY. Methods for inhibiting or preventing degradation include, but are not limited to, treatment of the biological sample with protease or RNAase inhibitors, freezing the biological sample, or placing the biological sample on ice. Preferably, prior to analysis, the biological samples or isolates are constantly kept under conditions as to prevent degradation of protein or RNA, e.g., the biomarkers of the present invention.

In embodiments requiring use RNA, for the detection methods of the present invention, the nucleic acids may be isolated from the biological sample. Nucleic acid molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994).

A variety of RNA detection methods are also known that can be used to detect TROY expression at the nucleic acid level. Methods for detecting levels of mRNA are well known to those skilled in the art. For example, detection of RNA transcripts may be achieved by Northern blotting, wherein a preparation of RNA is analyzed on a denaturing agarose gel, and transferred to a suitable support, such as activated cellulose, nitrocellulose or glass or nylon membranes. Labeled (e.g., radiolabeled, enzyme labeled or fluorescently labeled) cDNA or RNA is then hybridized to the preparation, washed and analyzed by methods such as autoradiography. Methods to generate probes for hybridization based on the known sequence of the mRNA encoding TROY are well known to the skilled artisan.

Detection of RNA transcripts can further be accomplished using known amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap lipase chain reaction (RT-AGLCR) as described by R. L. Marshall, et al., PCR Methods and Applications 4: 80-84 (1994). Methods to generate primes for amplification based on the known nucleic acid sequence of the gene of interest are well know to the skilled artisan. Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO 9322461.

In situ hybridization visualization may also be employed, wherein a radioactively labeled antisense RNA probe is hybridized with a thin section of a biological sample, such as a biopsy sample, washed, cleaved with RNase and exposed to a sensitive emulsion for autoradiography. The samples may be stained with haematoxylin to demonstrate the histological composition of the sample, and dark field imaging with a suitable light filter shows the developed emulsion. Non-radioactive labels such as digoxigenin may also be used.

Alternatively, RNA expression can be detected on a DNA array, chip or a microarray. One or more oligonucleotides corresponding to the nucleic acid encoding TROY are immobilized on a chip which is then hybridized with labeled nucleic acids of a test sample obtained from an individual. Positive hybridization signal is obtained with the sample containing transcripts encoding TROY. Methods of preparing DNA arrays and their use are well known in the art. (See, for example U.S. Pat. Nos. 6,618,6796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug discovery Today 5: 59-65, which are herein incorporated by reference in their entirety). Serial Analysis of Gene Expression (SAGE) can also be performed (See for example U.S. Patent Application 20030215858).

One may also monitor RNA levels during the treatment efficacy for or prognosis of melanoma by, for example, taking several biological samples at time intervals from the individual being treated. To monitor mRNA levels, for example, mRNA is extracted from the biological sample to be tested, reverse transcribed, and fluorescent-labeled cDNA probes are generated. The microarrays capable of hybridizing to the cDNA of TROY, are then probed with the labeled cDNA probes, the slides scanned and fluorescence intensity measured. This intensity correlates with the hybridization intensity and expression levels.

In another embodiment, RNA-FISH is used to determine TROY transcripts in a sample. Fluorescence in situ hybridization (FISH) is known to those of skill in the art (see Angerer, 1987 Meth. Enzymol., 152: 649). Generally, in situ hybridization comprises the following major steps: (1) fixation of tissue or biological structure to be analyzed; (2) prehybridization treatment of the biological structure to increase accessibility of target RNA, and to reduce nonspecific binding; (3) hybridization of the mixture of nucleic acids to the nucleic acid in the biological structure or tissue; (4) posthybridization washes to remove nucleic acid fragments not bound in the hybridization, and (5) detection of the hybridized nucleic acid fragments.

In a typical in situ hybridization assay, cells or tissue sections are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets, e.g., cells, are then typically washed at a predetermined stringency or at an increasing stringency until an appropriate signal to noise ratio is obtained.

The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Stringent conditions are well known by those skilled in the art.

In some applications it is necessary to block the hybridization capacity of repetitive sequences. Thus, in some embodiments, tRNA, human genomic DNA, salmon sperm DNA or Cot-1 DNA is used to block non-specific hybridization. TROY peptide or protein can also be detected, including measuring protein levels. In one embodiment, protein, e.g., TROY resistance biomarkers of the present invention, is detected by contacting the biological sample with an antibody-based binding moiety that specifically binds to TROY, or to a fragment of TROY. Formation of the antibody-protein complex is then detected and may be measured to indicate protein levels.

The term "antibody-based binding moiety" or "antibody" includes immunoglobulin molecules and immunologically active determinants of immunoglobulin molecules, e.g., molecules that contain an antigen binding site which specifically binds (immunoreacts with) to the protein of interest, e.g., TROY resistance biomarkers of the present invention. The term "antibody-based binding moiety" is intended to include whole antibodies, e.g., of any isotype (IgG, IgA, IgM, IgE, etc), and includes fragments thereof which are also specifically reactive with TROY. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's may be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled.

"Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS.

In the methods of the invention that use antibody based binding moieties for the detection of TROY, the level of TROY protein present in the biological samples correlates to the intensity of the signal emitted from the detectably labeled antibody.

In one preferred embodiment, the antibody-based binding moiety is detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. Chemiluminescence is another method that can be used to detect an antibody-based binding moiety.

Detection may also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by autoradiography. Isotopes which are particularly useful for the purpose of the present invention are $^3$H, $^{131}$I, $^{35}$S, $^{14}$C, and $^{125}$I.

It is also possible to label an antibody with a fluorescent compound. When the fluorescently labeled antibody is exposed to light of the proper wave length, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, TROY protein can be detected by immunoassays, such as enzyme linked immunoabsorbent assay (ELISA), radioimmunoassay (RIA), Immunoradiometric assay (IRMA), Western blotting, or immunohistochemistry, each of which are described in more detail below. Immunoassays such as ELISA or RIA, which can be extremely rapid, are more generally preferred. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

"Radioimmunoassay" is a technique for detecting and measuring the concentration of an antigen using a labeled, e.g. radioactively labeled, form of the antigen. Examples of radioactive labels for antigens include 3H, 0.14C, and 125I. The concentration of TROY antigen in a biological sample is measured by having the antigen in the biological sample compete with the labeled, e.g. radioactively, antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." ELISA is a technique for detecting and measuring the concentration of an antigen using a labeled, e.g., enzyme linked, form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody against the TROY is linked to a solid phase, for example, a microtiter plate, and exposed to a biological sample containing TROY antigen. The solid phase is then washed to remove unbound antigen. A labeled antibody, e.g. enzyme linked, is then bound to the bound-antigen, if present, forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing TROY. The TROY-antibody mixture is then contacted with a solid phase, e.g. a microtiter plate, that is coated with TROY. The more antigen is present in the sample, the less free antibody that will be available to bind to the solid phase. A labeled, e.g., enzyme linked, secondary antibody is then added to the solid phase to determine the amount of primary antibody bound to the solid phase.

Alternatively, TROY expression in cells and/or tumors can be detected in vivo in a subject individual by introducing into the individual a labeled antibody against TROY. For example, the antibody can be labeled with a radioactive marker whose presence and location in a subject can be detected by standard imaging techniques.

In one embodiment, immunohistochemistry ("IHC") and immunocytochemistry ("ICC") techniques, for example, may be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of a specific antibody, wherein antibodies are used to specifically target molecules inside or on the surface of cells. The antibody typically contains a marker that will undergo a biochemical reaction, and thereby experience a change color, upon encountering the targeted molecules. In some instances, signal amplification may be integrated into the particular protocol, wherein a secondary antibody, that includes the marker stain, follows the application of a primary specific antibody.

Immunohistochemical assays are known to those of skill in the art (e.g., see Jalkanen, et al., J. Cell. Biol. 101:976-985 (1985); Jalkanen, et al., J. Cell. Biol. 105:3087-3096 (1987).

Typically, for immunohistochemistry, tissue sections are obtained from a patient and fixed by a suitable fixing agent such as alcohol, acetone, and paraformaldehyde, to which is reacted an antibody. Conventional methods for immunohistochemistry are described in Harlow and Lane (eds) (1988) In "Antibodies A Laboratory Manual", Cold Spring Harbor Press, Cold Spring Harbor, N.Y.; Ausbel et al (eds) (1987), in Current Protocols In Molecular Biology, John Wiley and Sons (New York, N.Y.). Biological samples appropriate for such detection assays include, but are not limited to, cells, tissue biopsy, whole blood, plasma, serum, sputum, cerebrospinal fluid, pleural fluid, urine and the like.

For direct labeling techniques, a labeled antibody is utilized. For indirect labeling techniques, the sample is further reacted with a labeled substance.

Alternatively, immunocytochemistry may be utilized. In general, cells are obtained from a patient and fixed by a suitable fixing agent such as alcohol, acetone, and paraformaldehyde, to which is reacted an antibody. Methods of immunocytological staining of human samples is known to those of skill in the art and described, for example, in Brauer et al., 2001 (FASEB J, 15, 2689-2701), Smith-Swintosky et al., 1997.

Immunological methods of the present invention are advantageous because they require only small quantities of biological material. Such methods may be done at the cellular level and thereby necessitate a minimum of one cell. Preferably, several cells are obtained from a patient affected with or at risk for developing cancer and assayed according to the methods of the present invention.

Other techniques may be used to detect TROY in a biological sample according to a practitioner's preference, based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Detectably labeled antibodies, e.g., antibodies against TROY or antigenic fragments thereof can then be used to detect and/or assess levels of the TROY protein, where the intensity of the signal from the detectable label corresponds to the amount of TROY present. Levels can be quantified, for example by densitometry.

In addition, TROY protein may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Nat). Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of TROY will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules, including TROY. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer, e.g., desorption source, mass analyzer, detect, etc., and varied sample preparations can be combined with other suitable components or preparations described herein, or to those known in the art. For example, in some embodiments a control sample may contain heavy atoms, e.g. $^{13}C$, thereby permitting the test sample to mixed with the known control sample in the same mass spectrometry run.

In one preferred embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantify the amount of the biomolecule present in the first sample. In certain embodiments, the identity of the biomolecules in the first and second sample can also be determined.

In one embodiment, TROY is detected by MALDI-TOF mass spectrometry.

The antibodies for use in the present invention may be obtained from a commercial source. Alternatively, antibodies can be raised against the full length polypeptide, or a portion of polypeptide of TROY.

Antibodies for use in the present invention can be produced using standard methods to produce antibodies, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., J. Immunology, (1990) 35: 1-21; and Kozbor et al., Immunology Today (1983) 4:72). Antibodies can also be readily obtained by using antigenic portions of the protein to screen an antibody library, such as a phage display library by methods well known in the art. For example, U.S. Pat. No. 5,702,892 (U.S.A. Health & Human Services) and WO 01/18058 (Novopharm Biotech Inc.) disclose bacteriophage display libraries and selection methods for producing antibody binding domain fragments.

In one embodiment, the methods of the present invention may be performed concurrently with methods of detection for other analytes, e.g., other mRNAs or proteins or small molecules, e.g., other markers associated with cancer risk, e.g., other markers associated with increased melanoma risk, in the biological sample from the individual.

The invention also provides a serum-based test to detect circulating melanoma cells in patients with this disease (we already have established RT-PCR methods that can detect TROY in cultured melanoma cells). Another issue is that we need to improve upon the commercial antisera, because currently we have to stain over night, when 2-3 hr incubation time is desirable for practical use by pathologists. However, the latter is considered more of a technical issue by the PI.

Accordingly, the invention provides TROY, and fragments thereof, as a novel melanoma-associated antigen. The invention provides methods of prognosis and diagnosis of cancer, particularly, melanoma, by detecting TROY in the biological sample form an individual who is in need of diagnosis or prognosis of a tumor, such as melanoma or metastatic tumors originating from melanoma.

One can also use TROY detection in vivo by labeling an antibody against an immunogenic fragment of TROY with an agent that can be detected in, for example contrast enhanced magnetic resonance imaging (MRI). In such method, one injects the labeled antibody against TROY in the blood circulation and the label concentrates into the areas wherein TROY is expressed. The method is particularly useful in detecting metastatic cells that originate from the primary tumor.

In contrast enhanced MRI, paramagnetic contrast agents are used to improve the detection of tissues, such as tumor masses. Monoclonal antibodies (McAb) have been used successfully in nuclear medicine for localization of tumors. Paramagnetic (Gd3+) labeled antibodies, in the case of the present invention, antibodies directed against TROY or an antigenic fragment thereof, can be used in several ways: 1) one can attach paramagnetic ions to the McAb; 2) one can attach several paramagnetic ions to a macromolecule that in turn is attached to a McAb; 3) one can also use a mixture of antibodies with an affinity to many antigenic sites per cell; and 4) one can use superparamagnetic particle attached to the McAb. All these methods are well known to a skilled artisan.

Accordingly, the invention provides a method of diagnosis of or diagnosing a non-epithelial cell cancer, such as melanoma, comprising analyzing or determining in a biological sample the presence, absence or the amount of TROY expression, wherein increase in the TROY expression in the biological sample is indicative of the biological sample containing a population of malignant non-epithelial cells. Alternatively, presence of TROY can be indicative of the biological sample containing malignant cells, such as malignant melanoma cells. This is particularly the case if TROY expression is detected in a tissue sample by labeling TROY with an antibody or a nucleic acid probe that determines both the location as well as the amount of TROY in the biological sample. In one embodiment, the method of diagnosis is performed in vitro. In another embodiment, the method of diagnosis is performed in vivo, such as using contrast enhanced MRI.

In one embodiment, the malignant non-epithelial cell is a gliosarcoma or prostate cell. If detection is directed to these cells, it is preferable that one determines the level of expression and compares it to the level of expression in normal cells of the same biological origin.

In one embodiment, the biological sample is urine or blood sample, wherein presence of increased amount of TROY as compared to a similar sample from a control individual who does not carry malignant cells, is indicative of presence of malignant cells in the individual. One can also compare the sample from the individual to control samples that are taken from individuals with different types and/or stages of malignancies, such as different stages of melanoma, thus allowing one to match the individual sample with the control that most closely reflects the expression in the individual sample. This will allow not only diagnosis, but also prognosis of the disease based on the type and stage of cancer.

In one embodiment, the biological sample is a tissue biopsy sample, such as a skin biopsy or a prostate biopsy.

In one embodiment, one uses a probe, such as a monoclonal or polyclonal antibody or an antibody fragment, to determine the level of expression of TROY, for example in an immunohistochemical method. One can also use the method of any of the preceding claims, wherein the analyzing of the biological sample for TROY expression comprises using a probe that specifically binds an immunogenic fragment of the TROY protein, preferably human TROY protein. Such fragments can be produced using TROY peptide sequence. One can use either of the known splice variants of TROY.

In another embodiment, one analyzes TROY expression using a probe that specifically binds the TROY encoding nucleic acid. In such cases, one can use either in situ analysis using a probe that binds TROY encoding mRNA in a cell sample or in a Northern blot hybridization analysis, or a nucleic acid amplification-based method such as RT-PCT.

Therapeutic Methods

The invention is also useful for developing antibody-based therapeutic approaches to treating breast cancer, similarly to, for example, HERCEPTIN® (Trastuzumab). We have shown that TROY is a cell surface receptor that is accessible to antibodies in cancer treatment. TROY or TROY-derived peptides can naturally also be modified to enhance binding by antibodies, and/or binding to MHC class I and recognition by cytotoxic T cells in immunotherapy.

We have also shown that TROY is also a negative regulator of axonal regeneration in the brain. Specific drugs can be developed modeled on the predicted structure of TROY to activate the receptor, and cause cell death of the TROY-expressing tumor cell.

Melanoma is relatively rare compared to, for example, breast cancer, striking only about 1 in 80 people, but it receives a lot of attention because there are no effective treatments for an advanced disease. New treatments could also help in prevention of relapse or development of primary tumors in high-risk patients, such as those with Stage II disease. There are at least three conceivable, different strategies that take advantage of TROY-associated expression and function on the cell surface of melanoma cells. Following the teachings of this invention, one can now develop drugs which can modulate the activity of this receptor which may result in tumor cell death or growth-arrest. In addition to diagnostic and prognostic antibodies, one can now generate therapeutic antibodies against TROY and immunogenic fragments thereof. Such antibodies can be used in an antibody treatment regimen against cancers which express this gene similar to, for example, HERCEPTIN, in breast cancer.

The present invention of targeting TROY can also be combined with other techniques that can be used to treat cancers, such as melanoma, such as using targeting of other tumor associated antigens, chemotherapy, radiation and surgery.

The term "TROY-targeting agent" as used herein and throughout the specification and the claims encompasses antibodies, antibody fragments and the like that can target TROY or a fragment thereof, antisense oligonucleotides, RNA interfering agents, such as siRNA, aptamers and small molecules that have been designed to target TROY. Compounds that specifically target TROY, whether detected in vivo or in vitro, can be selected using techniques known in the art and discussed herein. Candidate drug screening assays may be used to identify bioactive candidate agents that inhibit the activity of the TROY. Of particular interest are screening assays for agents that have a low toxicity for human cells. A wide variety of assays may be used for this purpose, including labeled in vitro protein-protein binding assays, electrophoretic mobility shift assays, enzyme activity assays, immunoassays for protein binding, and the like. Purified TROY protein may also be used for determination of three-dimensional crystal structure, which can be used for modeling intermolecular interactions, transporter function, etc. Such compounds may be, for example, inhibitors, antibodies, aptamers, siRNAs, and vectors that inhibit the taxol resistance activity of the biomarkers of the present invention. The TROY-targeting agents useful in the method of the present invention also include antibodies which interfere with TROY activity, including monoclonal, chimeric humanized, and recombinant antibodies and fragment thereof which are characterized by their ability to inhibit the TROY and which have low toxicity.

Neutralizing antibodies are readily raised in animals such as rabbits or mice by immunization with a biomarker. Immunized mice are particularly useful for providing sources of B cells for the manufacture of hybridomas, which in turn are cultured to produce large quantities of anti-biomarker monoclonal antibodies. Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

Humanized antibodies are immunoglobin molecules created by genetic engineering techniques in which the murine constant regions are replaced with human counterparts while retaining the murine antigen binding regions. The resulting mouse-human chimeric antibody should have reduced immunogenicity and improved pharmacokinetics in humans. Preferred examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923. Human antibodies can be prepared by known means such as using phage display libraries. In one embodiment, single chain antibodies are used.

In connection with the administration of TROY-targeting agent, a drug which is "effective against" a cancer indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

As used herein, the terms "effective" and "effectiveness" in connection with treatment includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like. The compounds of the invention can be administered parenterally by injection or by gradual infusion over time and can be delivered by peristaltic means.

Administration of the compositions comprising TROY-targeting agent may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics.

For topical administration, the pharmaceutical composition comprising TROY-targeting agent is formulated into ointments, salves, gels, or creams, as is generally known in the art.

The TROY-targeting agent containing compositions of this invention can be conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

Suitable pharmaceutically acceptable carriers for oral, rectal, topical or parenteral (including inhaled, subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

Additionally, one can generate cytotoxic T cells which specifically recognize MHC class I-restricted TROY antigens displayed by tumor cells for development of tumor vaccines. Such approach has been used in several clinical trials in melanoma using less specific melanoma-associated antigens.

Such approaches often involve administering TROY, or an antigenic epitope thereof, for example, a T-cell specific epitope thereof to an individual. The administration is preferably done as at least two intervals, with some time between the administrations, such as about one, 2, 3, 4, 5, 6, 7, days apart or about 2, 3, 4, 5, 6, 7, 8, 9, 10, weeks apart or about 1, 2, 3, 4, 5, 6, 7, 8, 9, 10 or more months apart. Such approaches are called prime-boost applications and are well described in the art, for example, in Kaufman et al. (Journal of Clinical Oncology, Vol 22, No 11 (Jun. 1), 2004: pp. 2122-2132).

One can also use viral vectors, for example pox-viral vectors encoding TROY or antigenic epitopes thereof, to induce a T-cell response in the individual that the vector is administered into. For example, one can use recombinant vaccinia virus vectors. In the prime-boost administration, one preferably uses pox-virus vectors from different species in the prime and boost. For example, the prime can be administered with a vaccinia vector encoding the TROY epitope, and the boos administered with a fowl pox vector encoding the TROY epitope. (See, e.g., Kaufman et al. Journal of Clinical Oncology, Vol 22, No 11 (Jun. 1), 2004: pp. 2122-2132).

Accordingly, the invention also provides use of anti-TROY agents, such as antibodies, antisense nucleic acids or RNA interfering agents, or a vaccine preparation that elicits a host immune response against cells expressing TROY in a medicament for melanoma.

In one embodiment, the invention provides method for treating a malignant non-epithelial cell tumor comprising administering to an individual having malignant non-epithelial cell tumor cells expressing TROY in a pharmaceutically acceptable or pharmaceutical carrier with a TROY-targeting agent mixed with it.

In one embodiment, the TROY-targeting agent is an antibody or an antibody fragment generated against TROY or an antigenic fragment of TROY or a combination thereof.

In one embodiment, the TROY-targeting agent induces a TROY-targeting T-cell response in the individual. In one embodiment, the TROY-targeting agent is a TROY peptide or a T-cell response inducing fragment of a TROY that specifically binds to a functional region in TROY.

In one embodiment, the functional region of TROY is TRAF1, TRAF2, TRAF3, TRAF4, TRAF5, or TRAF6 binding region. In a preferred embodiment, the functional region is TRAF-6 binding region of TROY.

In one embodiment, the TROY-targeting agent is a TROY peptide or a T cell response inducing fragment of a TROY is encoded by at least one vector, such as a pox virus vector.

In one embodiment, one administers a first pox virus vector encoding a TROY peptide or a T-cell response inducing fragment of a TROY peptide and after a time interval, such as 1, 2, 3, 4, 5, 6, 7, 8, 9, 10 11, or 12 weeks or 4, 5, 6, 7, 8, 9, 10, 11, 12 months, one administers a second pox virus vector encoding a TROY peptide or a T-cell response inducing fragment of a TROY. In a preferred embodiment, the first and second pox virus vectors are from different species than the first pox virus vector. Use of tumor associated antigens has been well described in the literature and similar methods can be easily tested for efficacy in melanoma based on our finding that TROY is a highly specific malignant melanoma marker.

EXAMPLES

Materials and Methods

Cell Cultures. Primary melanocytes were obtained from Cambrex Bio Science (Rockland, Me.) and maintained in manufacturer's melanocyte growth media. Primary melanoma cells were derived by Dr. Byers (11) and maintained in Dulbecco's modified Eagle's medium with 8% (vol/vol) calf serum and 2% fetal calf serum (FCS). Established cell lines were obtained from the American Type Culture Collection (Manassas, Va.) and grown in Dulbecco's modified Eagle's medium with 10% (vol/vol) FCS at 37° C. in 5% $CO_2$ in humidified air.

Northern and Western blot Analysis. RNA was extracted using Trizol reagent (Invitrogen, Carlsbad, Calif.) and subjected to electrophoresis through a denaturing formaldehyde-agarose gel (1.6%). Other procedures, including generation of [32P]-labeled cDNA probes, were done as described (4). For Western blot analysis, 105 SK-Mel-2 cells were lysed in protein loading buffer and immunoblotted as described (4). TROY/TAJ expression was determined using anti-TROY/TAJ antibody (1:100) and βActin by anti-actin antibody (1:2000) followed by visualization with HRP-coupled secondary antibody (1:2500) (Santa Cruz, Santa Cruz, Calif.) and ECL-plus reagent (GE Healthcare Bio-Sciences, Piscataway, N.J.) as described (4).

RT-PCR Assay. 1 μg RNA was used for reverse transcriptase (RT) reactions according to the manufacturer's protocol (Superscript First-Strand Synthesis System, Invitrogen, Carlsbad, Calif.). PCR conditions for amplification of TROY/TAJ and βActin were: 2 min at 94° C., and then 40 and 35 cycles, respectively, of 1 min at 94° C., 1 min at 56° C. and 2 min at 72° C. Primer sequences are: TROY/TAJ, forward: 5'-GCAAGAATTCAGGGATCOGTCTGG (SEQ ID NO.: 1), reverse: 5'-AGCGCTGCAGATAACGGCAGCCAG (SEQ ID NO.: 2). βActin primers have been described (4).

RNA Interference (siRNA), Transfections and [$^3$H]-Thymidine Incorporation Assay. 2.5×10$^5$ SK-Mel-2 cells plated in 6-well plates were transfected using LIPOFECTAMINE PLUS™ according to the manufacturer's protocol (Invitrogen, Carlsbad, Calif.) with 30 nM scrambled control siRNA or siRNA (Ambion, Austin, Calif.) targeting hTROY/TAJ exon 3 (Genbank: NM_148957)/exon 2 (Genbank: NM_018647). After 6 h, cells received complete media and allowed to recover for 24 h. Cells were then serum-starved for 16 h, after which they received complete media containing 1 μCi [3H]-thymidine for 10 h. Next, cells were fixed in 5% TCA, lysed in 0.5 M NaOH/0.5% SDS and radioactive nucleotide incorporation was determined in a scintillation counter, or they were prepared for Western blot analysis.

Antibodies, Tissues and Immunohistochemical Analysis. IRB approval was obtained prior to all studies involving patient materials. Only specimens that were ≧1 mm$^3$ with ≧10% tumor cells and ≦30% necrosis were included. Paraffin embedded sections: Eleven paraffin embedded melanomas taken from cases at Skin Pathology Laboratory, Department of Dermatology, Boston University were cut at 4 μM and incubated overnight at room temp with anti-Troy/TAJ antibody (1:20; Santa Cruz, Calif.). Next, an IgG-AP polymer labeled secondary antibody was applied and incubated for two hours followed by staining with liquid permanent red (Dakocytomation, Carpinteria, Calif.). Samples were also stained with anti-HMB-45 antibody (1:100, Dakocytomation Carpinteria, Calif.) for 32 min on a Ventana Benchmark LT with enhanced v-red detection kit (Ventana Medical Systems, Tucson, Ariz.). MART-1 staining was done after microwave antigen retrieval with anti-MART-1 antibody (Santa Cruz, Santa Cruz, Calif.) using a MACH 4 UNIVERSAL POLYMER DETECTION system with diaminobenzidine as chromogen according to the manufacturer's instructions (Biocare, Concord, Calif.). Frozen sections: 34 fresh frozen melanomas were obtained from the Cooperative Breast Cancer Tissue Resource (NCI). Other investigators may have received the same tumors. In addition, six basal cell carcinomas (BCC) and ten normal appearing skin samples adjacent to BCC taken from Moh's surgery at the Department of Dermatology, Boston University Medical Center were embedded in OCT (Sakura Finetek, Torrance, Calif.), cut at 5 μM and fixed in acetone. Slides were then immunostained with our own anti-TROY/TAJ antibody for 32 min at 1:10 on the Ventana Benchmark LT using the enhanced v-red detection kit (Ventana Medical Systems, Tucson, Ariz.). This antibody was raised by immunization of rabbits with a TROY/TAJ-peptide located in its N-terminus (Qbiogene, Carlsbad, Calif.). Serum was affinity-purified against peptide (Arista Biologicals, Allentown, Pa.) and verified by ELISA. In addition, ten melanoma samples were co-stained with anti-TRAF6 antibody (Santa Cruz, Santa Cruz, Calif.) at 1:20 for 32 min using the same techniques. Cell lines: Two cell lines representing a primary and a metastatic melanoma (11) were grown on glass slides, fixed in acetone and immunostained with anti-TROY/TAJ antibody (1:20, Santa Cruz, Santa Cruz, Calif.) as described above.

Skin cell culture: Keratinocyte cultures which contain some melanocytes were obtained by cutting foreskin into 1 mm squares and incubating for 45 min at 37° C. and then overnight in 0.25% trypsin at 4° C. Next, epidermis was separated from the dermis and primary cultures were obtained by placing keratinocytes in primary keratinocyte media (12).

Results and Discussion

Figure 1:
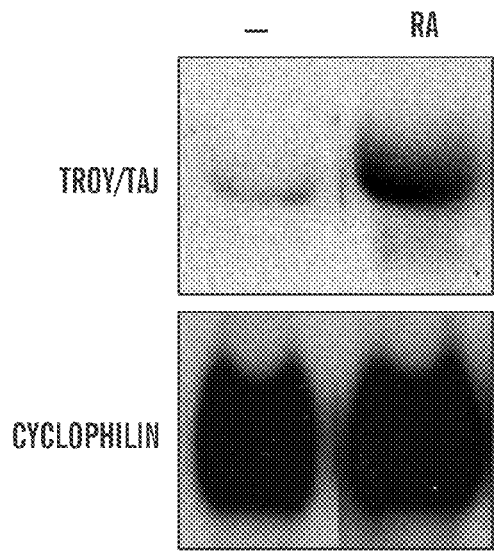
FIG. 1 shows a Northern blot hybridization assay (20 μg RNA/lane) showing that TROY is a novel RA-induced gene in S91 murine melanoma cells. Cells were treated for 16 hr with 1 μM RA or 0.1% DMSO vehicle control. C serves as loading control.

TROY Is a Novel RA-Regulated Gene in S91 Melanoma Cells. During a genetic screen for melanoma-associated genes that may be important for growth and differentiation in murine S91 cells (4) we identified TROY as a novel retinoic acid (RA)-regulated gene, as shown in a Northern blot analysis in FIG. 1. During mouse embryogenesis, TROY is detected in many tissues, but in adult animals expression becomes highly restricted to hair follicles and neuron-like cells in specific brain regions (5, 10, 13-15), and perhaps also in humans prostate (6). RA has been shown to induce TNFα receptors in neuroblastoma cells (16), but this is the first example of TROY or any other TNFSFR member that is induced in melanoma cells.

Figure 2:
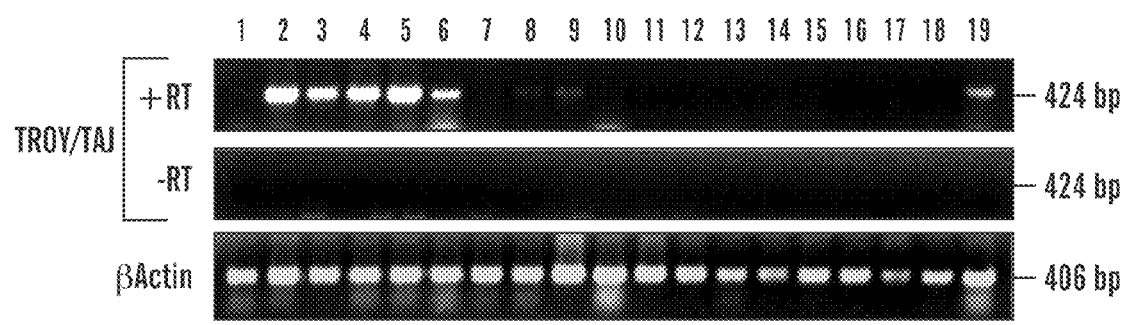
FIG. 2 shows that an RT-PCR assay readily detects TROY mRNA in all human melanoma cell lines, but no or very low levels in normal primary melanocytes, or non-related tumor cell lines. Embryonic 293 cells serve as positive control. −, no detectable expression; −/+, very low expression; +, low expression; ++, moderately high expression; +++, high expression. RT-panel shows lack of product in control reaction without added RT. SCC, squamous cell carcinoma.

TROY RNA Is Specifically Detected in Melanoma Cell Lines. TNFRSF members control signaling pathways for cell proliferation, differentiation and apoptosis, processes that shape development and the immune system but which also play a role in carcinogenesis (17). Thus our finding that TROY is expressed in this cell line is interesting for melanoma biology. To assess its relevance for human disease, we first wanted to verify that TROY is expressed in human melanoma in a RA-independent manner. We also wanted to know whether TROY is expressed in melanocytes or other, malignant cells. To address these issues, we used RT-PCR techniques to determine relative TROY RNA expression levels in a panel of cell lines that were cultured in the absence of RA. FIG. 2 shows that primary melanocytes do not express detectable TROY RNA, nor do any of the other established cancer cells, although two breast cancer cell lines expressed very low levels. In contrast, all five melanoma cell lines expressed moderate to high levels of TROY RNA, independent of their pigmentation status. The magnitude of TROY expression is substantial because 293 cells, which represent one of the few cell lines that express TROY, in accordance with their embryonic lineage (7), have lower levels than the melanoma cells. These results show that TROY is not normally expressed in melanocytes however, it is aberrantly re-expressed at high levels in melanoma, but not other epithelial cancers.

TROY Protein Is Expressed With High Specificity in Melanoma. Next, we wanted to validate and expand upon our previous experiments by performing an immunohistochemical analysis of TROY expression in primary melanoma cells and melanoma patient samples, compared with normal skin biopsies and primary skin cell cultures. Our results are illustrated and summarized in FIG. 3. Consistent with our in vitro studies, 0/10 (0%) of normal skin biopsies (FIG. 3A, panel 1), cultured skin keratinocytes mixed with normal melanocytes (FIG. 3A, panel 2) as well as 0/6 (0%) of basal cell carcinomas (BCC) as a representative, non-melanoma skin cancer (FIG. 3A, panel 3) showed any detectable TROY expression. Curiously, however, we found moderately strong TROY-staining of germinative cells in sebaceous glands (FIG. 3A, panel 4). This observation had not been reported from mouse expression studies. However, sebaceous glands develop as an appendix from the developing hair follicle (17), a site of known TROY expression in adult mice (5). In sharp contrast, both primary cell lines derived from a primary and a metastatic tumor stained strongly positive for TROY (FIG. 3B, panels 1 and 2, respectively). Moreover, analysis of all primary and metastatic melanoma patient samples showed that 45/45 (100%) samples were TROY-positive with typically high levels of expression in individual tumor cells as illustrated for a metastatic tumor in FIG. 3C, panels 1, 2.

For comparison, a serial section of this tumor was also stained for two widely-used melanoma biomarkers. The HMB-45 antigen is thought to be a sialylated glycoprotein (gp100) that is also present on normal melanocytes. Melanoma Antigen Recognized by T cells (MART)-1 is a melanocyte differentiation antigen that is recognized by cytotoxic T cells in a MHC class I-restricted fashion. Like HBM-45, not only is MART-1 expressed in most, but not all, melanomas, it is also expressed in normal melanocytes and benign nevi, as well as in certain steroid-producing tumors (18,19). Antibodies against HMB-45 and MART-1 stain this tumor with about the same intensity as TROY (FIG. 3C, panels 3 and 4, respectively).

These results are in agreement with our RT-PCR analysis, and show that TROY is a novel, highly melanoma-specific gene that is not expressed in benign melanocytes or other skin cells, nor is it expressed in non-melanoma skin cancer.

TRAF-6 Is Co-Expressed With TROY. Next we wanted to establish whether TROY is functionally important for melanoma. There is no known ligand for TROY (7), so we addressed this issue in the following manner. TNFR-associated factors (TRAFs) are important adapter molecules for various TNFRs. TROY was shown to bind with and/or signal through TRAF-1, TRAF-2, TRAF-3, TRAF-5 and TRAF-6 (5,6). These results suggest a rather redundant signaling cascade, however we were particularly interested in TRAF-6 because TRAF-6-deficient mice display HED (8) and abnormalities in tooth development (20), a known site of TROY-expression during mouse embryogenesis (13,20). Moreover, TRAF-6 plays an important role in JNK activation by related XEDAR, and JNK is also activated by forced expression of TROY (6,8,9). Thus, we focused on TRAF-6 as a major indicator of functional TROY-signaling, and serial sections of metastatic melanoma tissues were stained with anti-TROY and anti-TRAF-6 antibodies, as shown in FIG. 3D, panels 1 and 2, respectively. TROY and TRAF-6 are co-expressed in 10/10 (100%) cases, and without wishing to be bound by a theory, we suggest that the TROY-TRAF-6-signaling axis is therefore functional in melanoma cells.

TROY Contributes to Melanoma Growth. Earlier reports showed that transiently transfected TROY resulted in caspase-independent programmed cell death in some, but not all, cell types. This mechanism may involve different TRAFs and is possibly mediated through activation of JNK (6,8,9), but not NFκ-B (6). However, the physiological relevance of these observations remains uncertain and since melanoma cells generally grow well, a significant pro-apoptotic role can likely be excluded. A more conceivable effect may be stimulation of tumor growth, as some TNFRSF members are known to do (17). Indeed, it was already suggested that TROY may control precursor cell proliferation or maintenance of the undifferentiated state during development of neuroepithelial cells (15). To study the possible reason why TROY would be re-expressed in melanoma cells, TROY-positive SK-Mel-2 cells (FIG. 2) were transfected with a control siRNA or a siRNA that effectively suppresses endogenous TROY (FIG. 4, top). Next, proliferation of cells with normal (high) and suppressed levels of TROY were determined by [$^3$H]-thymidine incorporation assay. As shown in FIG. 4 (bottom), DNA replication is strongly reduced by about 50% in TROY-depleted cells compared to control cells. This result shows that TROY performs an important growth-promoting role in melanoma, and without wishing to be bound by a theory, this is possibly via TRAF-6 as suggested by the data in FIG. 3D.

TROY Is a Novel, Highly-Specific Melanoma Biomarker That Provides a Unique Cell Surface Target. Melanoma is extremely dangerous because of its propensity to metastasize, and correct diagnosis and early detection of micrometastases are of critical importance. A variety of techniques are available for this purpose (18), but immunohistochemistry is generally favored. However, this methodology depends on the reliability, specificity and sensitivity of the reagents used to detect melanoma markers. Many serum, molecular and immunohistochemical factors have been analyzed for their usefulness as diagnostic and/or prognostic melanoma biomarkers, but all suffer from various problems in a clinical setting (18,19). For instance, widely-used MART-1, HMB-45 and similar S100b can not distinguish between benign melanocytic lesions and melanoma (18,19). Our studies show that TROY is specifically associated with primary and metastatic melanomas, while normal melanocytes remain unstained. It appears therefore that TROY is an embryonic antigen that is aberrantly re-expressed in melanoma and as such, is an excellent novel biomarker for melanoma.

Our in vitro data shows that TROY contributes to tumor DNA replication, providing a satisfactory explanation for its re-expression and providing more insight into the genetic network that controls proliferation of these tumors. At the same time, our findings present a unique clinical opportunity. For instance, TROY antigen-bearing melanoma cells can now be targeted by both tumor-specific cytotoxic T cell as well as antibody-based therapies, the latter which is not currently feasible in this disease. In addition, small molecule inhibitors of TROY-signaling may be developed to slow tumor growth. One can detect and thus target TROY-expressing circulating serum melanoma cells by RT-PCR-based techniques (19).

REFERENCES

The references cited herein and throughout the specification, are herein incorporated by reference in their entirety.

1. Curtin J A, Fridlyand J, Kageshita T, et al. Distinct sets of genetic alterations in melanoma. N Engl J Med 2005; 353: 2135-47.
2. Parmiani G, Castelli C, Rivoltini L, et al. Immunotherapy of melanoma. Semin Cancer Biol 2003; 13:391-400.
3. Atallah E, Flaherty L. Treatment of metastatic malignant melanoma. Curr Treat Options Oncol 2005; 6:185-93.
4. Spanjaard R A, Lee P J, Sarkar S, Goedegebuure P S, Eberlein T J. Clone 10d/BM28 (CDCL1), an early S-phase protein, is an important growth regulator of melanoma. Cancer Res 1997; 57:5122-8.
5. Kojima T, Morikawa Y, Copeland N G, et al. TROY, a newly identified member of the tumor necrosis factor receptor superfamily, exhibits a homology with Edar and is expressed in embryonic skin and hair follicles. J Biol Chem 2000; 275:20742-7.
6. Eby M T, Jasmin A, Kumar A, Sharma K, Chaudhary P M. TAJ, a novel member of the tumor necrosis factor receptor family, activates the c-Jun N-terminal kinase pathway and mediates caspase-independent cell death. J Biol Chem 2000; 275:15336-42.
7. Hu S, Tamada K, Ni J, Vincenz C, Chen L. Characterization of TNFRSF19, a novel member of the tumor necrosis factor receptor superfamily. Genomics 1999; 62:103-7.
8. Naito A, Yoshida H, Nishioka E, et al. TRAF6-deficient mice display hypohidrotic ectodermal dysplasia. Proc Natl Acad Sci USA 2002; 99:8766-71.
9. Sinha S K, Zachariah S, Quinones H I, Shindo M, Chaudhary P M. Role of TRAF3 and -6 in the activation of the NF-kappa B and JNK pathways by X-linked ectodermal dysplasia receptor. J Biol Chem 2002; 277:44953-61.
10. Mandemakers W J, Barres B A. Axon regeneration: it's getting crowded at the gates of TROY. Curr Biol 2005; 15:R302-5.
11. Byers H R, Etoh T, Doherty J R, Sober A J, Mihm M C Jr. Cell migration and actin organization in cultured human primary, recurrent cutaneous and metastatic melanoma. Time-lapse and image analysis. Am J Pathol 1991; 139: 423-35.
12. Gilchrest B A. Relationship between actinic damage and chronologic aging in keratinocyte cultures of human skin. J Invest Dermatol 1979; 72:219-23.
13. Pispa J, Mikkola M L, Mustonen T, Thesleff 1. Ectodysplasin, Edar and TNFRSF19 are expressed in complementary and overlapping patterns during mouse embryogenesis. Gene Expr Patterns 2003; 3:675-9.
14. Hisaoka T, Morikawa Y, Kitamura T, Senba E. Expression of a member of tumor necrosis factor receptor superfamily, TROY, in the developing olfactory system. Glia 2004; 45:313-24.
15. Hisaoka T, Morikawa Y, Kitamura T, Senba E. Expression of a member of tumor necrosis factor receptor superfamily, TROY, in the developing mouse brain. Brain Res Dev Brain Res 2003; 143:105-9.
16. Chambaut-Guerin A M, Martinez M C, Hamimi C, Gauthereau X, Nunez J. Tumor necrosis factor receptors in neuroblastoma SKNBE cells and their regulation by retinoic acid. J Neurochem 1995; 65:537-44.
17. Locksley R M, Killeen N, Lenardo M J. The TNF and TNF receptor superfamilies: integrating mammalian biology. Cell 2001; 104:487-501.
18. Mangini J, Li N, Bhawan J. Immunohistochemical markers of melanocytic lesions: a review of their diagnostic usefulness. Am J Dermatopathol 2002; 24:270-81.
19. Li N, Mangini J, Bhawan J. New prognostic factors of cutaneous melanoma: a review of the literature. J Cutan Pathol 2002; 29:324-40.
20. Ohazama A, Courtney J M, Tucker A S, et al. Traf6 is essential for murine tooth cusp morphogenesis. Dev Dyn 2004; 229:131-5.

The invention claimed is:

1. A method of diagnosis of malignant melanoma comprising analyzing a biological sample from a subject in need of diagnosis of malignant melanoma for TROY expression, detecting and measuring the amount of the TROY expression in the biological sample, and diagnosing malignant melanoma in the subject if an increase in the TROY expression in the biological sample is detected compared to a control.

2. The method of claim 1, wherein the biological sample is serum or tissue sample.

3. The method of claim 1, wherein the biological sample is a tissue biopsy.

4. The method of claim 1, wherein the biological sample is urine.

5. The method of claim 1, wherein the biological sample is blood.

6. The method of claim 1, wherein analyzing of the biological sample for TROY expression comprises using a probe.

7. The method of claim 6, wherein the probe is an antibody that specifically binds an immunogenic fragment of the TROY protein.

8. The method of claim 6, wherein the probe is a nucleic acid probe that specifically binds to TROY encoding nucleic acid.

9. The method of claim 1, wherein the analyzing of the biological sample for TROY expression comprises use of nucleic acid amplification.

* * * * *